(12) United States Patent
Scherer et al.

(10) Patent No.: US 7,466,409 B2
(45) Date of Patent: Dec. 16, 2008

(54) METHOD AND APPARATUS FOR CMOS IMAGERS AND SPECTROSCOPY

(75) Inventors: Axel Scherer, Laguna Beach, CA (US); Mark Adams, Rockledge, FL (US)

(73) Assignee: California Institute of Technology, Pasadena, CA (US)

( * ) Notice: Subject to any disclaimer, the term of this patent is extended or adjusted under 35 U.S.C. 154(b) by 310 days.

(21) Appl. No.: 11/448,343

(22) Filed: Jun. 6, 2006

(65) Prior Publication Data

US 2007/0070347 A1 Mar. 29, 2007

Related U.S. Application Data

(60) Provisional application No. 60/688,643, filed on Jun. 8, 2005.

(51) Int. Cl.
*G01J 3/28* (2006.01)
(52) U.S. Cl. .................................................. 356/326
(58) Field of Classification Search ................ 356/326, 356/436, 440; 702/45, 49–50, 71
See application file for complete search history.

(56) References Cited

U.S. PATENT DOCUMENTS

| 7,245,373 B2 * | 7/2007 | Soller et al. ................. 356/325 |
| 2003/0133117 A1 * | 7/2003 | Chang ........................ 356/405 |
| 2003/0235924 A1 * | 12/2003 | Adams et al. ............... 436/172 |
| 2004/0233424 A1 * | 11/2004 | Lee et al. .................... 356/246 |

* cited by examiner

*Primary Examiner*—Kara E Geisel
*Assistant Examiner*—Abdullahi Nur
(74) *Attorney, Agent, or Firm*—Daniel L. Dawes

(57) ABSTRACT

A miniaturized fluidic spectrometer comprises a light source, a fluidic circuit having a plurality of flow channels through which an analyte flows, and a proximity detector array for detecting light from the light source transmitted through the fluidic circuit. Where the light source is broadband, a variable filter is disposed between the detector array and the fluidic circuit so that each position of the detector array is provided with a different wavelength response. The fluidic circuit is disposed in an optimized Fabry-Perot etalon. The fluidic circuit is defined in an elastomeric material and includes means for tuning the Fabry-Perot etalon by pressurization of flow channels in the elastomeric material.

16 Claims, 11 Drawing Sheets

METHOD AND APPARATUS FOR CMOS IMAGERS AND SPECTROSCOPY

RELATED APPLICATIONS

The present application is related to U.S. Provisional Patent Application Ser. No. 60/688,643, filed Jun. 8, 2005, which is incorporated herein by reference and to which priority is claimed pursuant to 35 USC 119.

GOVERNMENT RIGHTS

This invention was funded in part by support from the U.S. Army, contract grant no. DAAD19-00-1-0392. The Government has certain rights.

BACKGROUND OF THE INVENTION

1. Field of the Invention

The invention relates to the field of CMOS imagers and spectroscopy in miniaturized systems.

2. Description of the Prior Art

Over the past few years, the use of replication molding for the definition of microfluidic systems in elastomers has allowed the rapid development of compact analysis systems used for chemical sensing and biological diagnostics. For example, fluorescently activated cell sorters based on pumps, valves and channels defined in RTV silicone elastomers have demonstrated excellent throughput and sorting accuracy. These have been fabricated inexpensively into very small and robust microfluidic devices. Chemical surface pretreatment of specific areas within a flow channel has led to the possibility of developing very compact disease diagnostic chips, and even single molecule sizing systems can be built from elastomeric flow channels.

In all of these prior art applications, the overall size of the analysis system is typically limited by the dimensions of the optical excitation and detection components, and miniaturization of the read-out optics is therefore very desirable. However, miniaturization of grating-based spectrometer geometries ultimately is limited by a reduction of the spectral resolution, which can be predicted from the optical pathlengths between the grating and the detection slit. For example, multi-wavelength 4 mm by 12 mm spectrometers operating at 1500 nm typically yield a measured spectral resolution of approximately 1 nm.

This compromise between resolution, insertion losses and size has in the past limited the minimum size of such optical analysis systems. Much better spectral performance can be obtained by using dielectric filters, which can be directly deposited onto detector arrays to form multi-wavelength detector arrays. Such filtering has in the past been used for monolithic hyper-spectral imaging applications. Filtered detector arrays offer an inherent opportunity for the miniaturization of spectroscopic instruments in microfluidic applications, with the additional opportunity of obtaining low-resolution "lensless" images of the contents in the flow channel.

CMOS imagers were chosen for their ease of use and commercial availability. Imager elements based on CMOS technology also offer compatibility with other CMOS processes such as VLSI for integrating onboard signal processing.

One of the most important advantages of using elastomeric flow channels is the inherent transparency of the elastomer material in the visible wavelength range. Many semiconductor based microfluidic structures previously proposed have suffered from the inability to perform optical analysis of the device's contents in the visible and near-UV spectral ranges. Due to the absorption edge of silicon, for example, optical measurements in flow channels defined by this material are typically limited to the infrared range and visible/UV spectroscopy is virtually impossible to perform without using very elaborate geometries. For applications such as biochemistry, this poses a severe limitation since many absorption and fluorescence experiments are based on visible/UV fluorescent dyes. Silicone elastomers circumvent this problem since they are optically transparent and have similar UV absorption characteristics to those of glass. This property enables the easy integration of elastomer microfluidic devices with standard optoelectronic sources and detectors. Moreover, silicone elastomers are simple to integrate on top of already fully fabricated detector arrays, forming a hermetic seal to the passivation layer of the detector arrays.

Miniaturization of absorption spectrometers is expected to advance rapidly over the next few years, due to development of short wavelength LED'S and faster computer interconnects, as well as the development of inexpensive and high-quality CMOS imaging arrays.

BRIEF SUMMARY OF THE INVENTION

Fluorescence and absorption measurements of small quantities of fluids are typically made using microscopes, with light sources and images observed with lens systems. The illustrated embodiment discloses a method for further miniaturization and increased measurement sensitivity by integrating optical detector arrays with microfluidic channels. The channels, with lateral sizes of approximately 10-100 microns are directly aligned with the detector pixels onto detector arrays, such as are found in standard CMOS digital cameras, in which the sizes of the detectors range from 5-20 microns in lateral size. Near-field images of the transparent fluidic systems can be taken by using the CMOS imager through the deposited elastomer fluidics and as the size of the detector elements are substantially smaller than that of the channel, the channel can be observed with some contrast in these near-field images.

If a dielectric filter is introduced between the fluidic channels and the CMOS detector array, specific wavelengths can be filtered out and the described geometry can be used for spectroscopic purposes. For example, in fluorescence imaging, a filter can be designed to reflect the excitation beam to prevent that light from reaching the silicon detectors, whereas the fluorescent light can be transmitted through the dielectric multilayer filter to reach the detectors. Therefore, fluorescent images and fluorescence intensities can be measured from this geometry. The introduction of simple lenses between the fluorescence sources and the detector array can further improve the spatial resolution, although such a system would not be as compact.

An even simpler approach can be used to measure the absorption of the material in the fluidic channels. In this case, the CMOS imaging array can be used to image a light emitting diode or laser that illuminates the entire array. Again, fluidic channels are deposited onto this detector array. If a channel is filled with absorbing dye, the fluidic channel will appear darker than one filled with only water. Indeed, the amount of absorbing material can be measured by observing the contrast in the silicon detector image.

In all of these applications (both fluorescence and absorption), one of the main opportunities provided by integration of fluidics with detector arrays is that all of the detectors can be interrogated in parallel. This means that a single "snap-shot"

of the digital camera can be used to determine the absorption or fluorescence signals of many channels. This increases dramatically the speed with which data from multiple assays can be read, as a single "snapshot" of fluorescence or absorption will provide all of the information in the assay The detector arrays that can be used vary from conventional CMOS detector arrays that measure individual photocurrents and amplify these to avalanche photodiodes and low-noise PIN diodes. These all are able to be fabricated through conventional silicon technology, and commercially available with spacings to match the fluidic systems. For the purposes of this specification, all such detectors are expressly included, since some applications will require high-gain avalanche photodiodes and others require less expensive CMOS arrays or imagers.

Also, although the illustrated embodiment uses no lenses between the imaging array and the fluidic channels, it is sometimes of advantage to introduce an imaging lens. Therefore, the use of a compact system that includes a lens but takes advantage of the parallelism of multiple detector arrays to read out fluorescence or absorption on silicon detector chips is expressly contemplated as being within the scope of the invention.

In summary, the illustrated embodiment of the invention is directed to a miniaturized fluidic spectrometer comprising a light source, a fluidic circuit illuminated by the light source having a plurality of flow channels defined therein through which at least one analyte flows, and a proximity detector array disposed below the fluidic circuit for detecting light intensity from the light source transmitted through the fluidic circuit, including light that is transmitted through the flow channels in which the analyte flows.

In the preferred embodiment the detector array is a proximity CMOS imaging chip, but many other light detectors could be substituted.

In the preferred embodiment the light source is a broadband light source and the embodiment further comprises a variable filter disposed between the detector array and the fluidic circuit so that each position of the detector array is provided with a different wavelength response thereby providing a hyper-spectral imaging array.

The variable filter comprises a multilayer dielectric stack. The multilayer dielectric stack comprises a Fabry-Perot cavity. In particular, the Fabry-Perot cavity comprises a 2n+1 layer structure, a first n layers comprised of alternating layers of $Si_3N_4$ and $SiO_2$ of $\lambda/4$ thickness, a $\lambda/2$ thick layer of $SiO_2$, and n more layers alternating layers of $Si_3N_4$ and $SiO_2$ of $\lambda/4$ thickness. The variable filter is preferably grown on the fluidic circuit.

In another embodiment of the invention a fluorescent spectrum is obtained from an excitation frequency provided by the light source and the embodiment further comprises a blocking filter to reduce the excitation frequency from the imager, while permitting transmission of an emission frequency. The blocking filter is characterized by a varying spectral position of the reflectivity edge.

The detector array is an analog or digital imager. The spectrometer may further comprise a processor to geometrically normalize the light to the filter characteristics and to spectrally normalize the light source during data acquisition, and to compare each specific wavelength/area under test to a specific solvent reference flow channel in the fluidic circuit.

In one application of the invention the spectrometer further comprises a flow cytometer for fluorescence and/or absorption activated cell sorting.

In yet another embodiment the light source comprises an LED array and further comprises a high finesse optical cavity filter defined on LED array, which optical cavity filter is disposed directly on the fluidic circuit, which in turn is disposed on the detector array.

An embodiment of the spectrometer further comprises a Fabry-Perot etalon in which the fluidic circuit is disposed. The Fabry-Perot etalon is optimized for the fluid channel filled with water. The fluidic circuit is defined in an elastomeric material and the embodiment further comprises means for tuning the Fabry-Perot etalon by pressurization of flow channels in the elastomeric material.

The illustrated embodiment of the invention can also be defined as a method of performing spectroscopy with a CMOS detector array comprising the steps of radiating broadband light onto a flowing analyte in a fluidic circuit, variably filtering the light between the CMOS detector array and the fluidic circuit so that each position of the CMOS detector array is provided with a different wavelength response, and detecting transmission or absorbance of the light through flowing analyte using the CMOS proximity detector array disposed below the fluidic circuit, thereby providing a hyper-spectral imaging array.

The method further comprises the step of increasing the optical path length of light in the analyte in a fluidic circuit by multiply reflecting the light transmitted through the fluidic circuit before detecting transmission or absorbance of the light.

In yet another embodiment the invention is a method of performing spectroscopy with a detector array comprising the steps of radiating light onto a flowing analyte in a fluidic circuit, increasing the optical path length of light in the analyte in a fluidic circuit by multiply reflecting the light transmitted through the fluidic circuit before detecting transmission or absorbance of the light, and detecting transmission or absorbance of the light through flowing analyte using the detector array disposed below the fluidic circuit.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

Figure 1:
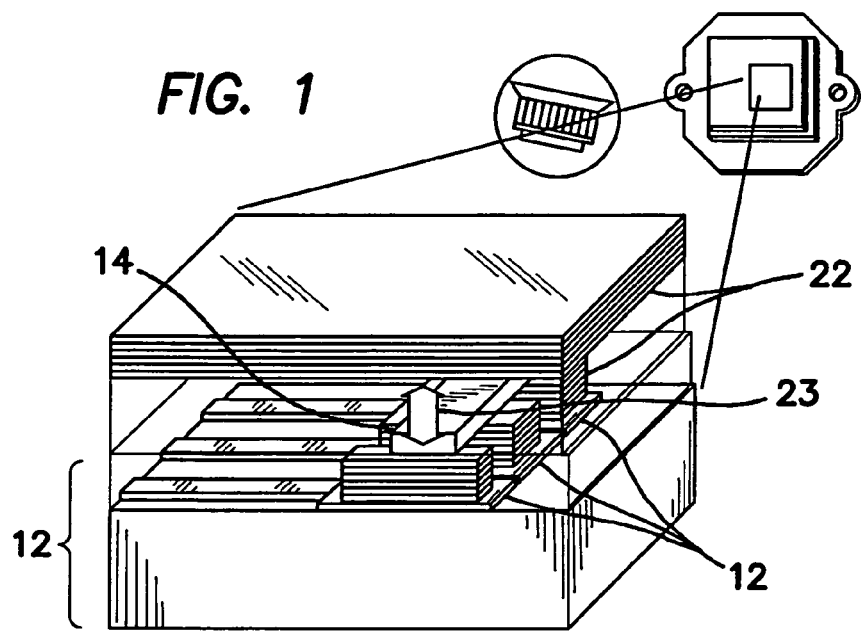
FIG. 1 is a perspective view of a spectroscopic measurement system according to the invention using a CMOS imager.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

CMOS Absorption Spectroscopy

Consider first the general concept of CMOS absorption spectroscopy. The external optical excitation and read-out devices described in the illustrated embodiment include a 588 nm light emitting diode 10 and a CMOS camera chip 12. One key difference between an absorption spectroscopy measurement system and a more conventional cell-sorting system is that no lenses are used for imaging in the absorption spectroscopy measurement system. This simple approach to reducing the size of a spectroscopic imaging system eliminates the need for focusing optics by placing the microfluidic devices 14 directly onto the CMOS camera chip or imaging detector array 12.

The imaging detector array 12 in one embodiment is comprised of silicon-based avalanche photodiodes (APDs), charge coupled devices (CCDs), or CMOS integrated p-n diode sensors. All of these devices are commercially available at reasonable costs. CCD arrays, although in general more sensitive, suffer from the need to read out the entire image information in order to determine intensity information from the pixels underneath the flow channels 14 in microfluidic devices 18. Avalanche photodiodes typically require larger areas, and thus significantly reduce the resolution of the imaging system. CMOS arrays 12, on the other hand, offer direct control over individual pixels, and, since most of the area of the image array 12 is typically not used, can provide much faster response times and long integration times. Although the lateral resolution of these arrays 12 cannot match that of an optical microscope, the lateral resolution is suitable for most visible spectroscopy applications on larger objects. It is to be expressly understood that any imaging devices now known or later devised may be substituted for those illustratively listed.

The highest resolution of such a proximity imaging system is determined by the pixel size on the imaging array 12, and can be less than 10 microns. The sensitivity of the imaging system is in turn dependent on the active area of the pixel, as well as leakage currents in the pixels. Other factors that determine the performance of an imaging detector array 12 in a spectrometer application are its sensitivity and dynamic range. The sensitivity becomes extremely important when examining picoliter volumes with a correspondingly small optical interaction length.

Figure 2A:
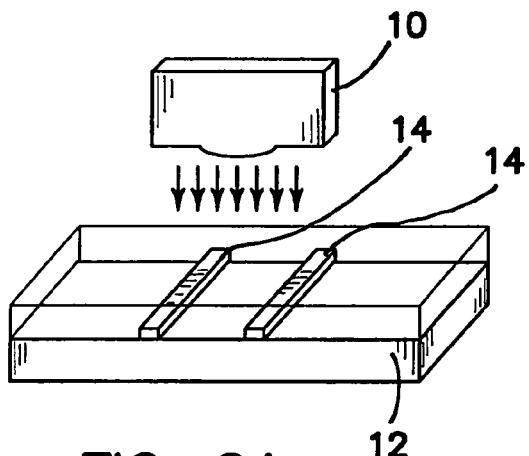
FIG. 2(a) is a perspective illustration showing how the absorption spectroscopy is performed.
Figure 2B:
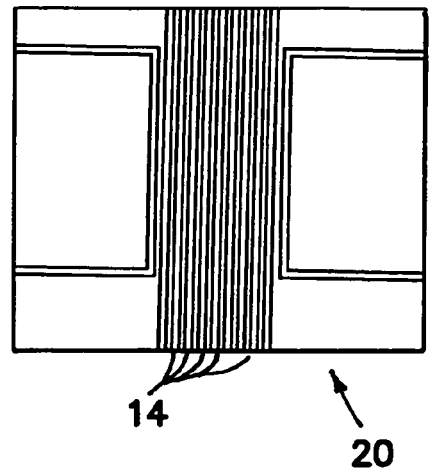
FIG. 2(b) is an enlarged plan view of a PDMS microfluidic chip imaged by the APS CMOS imager. The light source is a 588 nm Amax AlInGaP LED and the flow channels contain 7.5 mM to 30 µM bromophenol blue solutions. The far left channel is empty and the far right channel contains water for reference. This is an 8 bit image which is considerably less than the 12 bit resolution of the imager.

In the illustrated embodiment a CMOS imaging array 12 was chosen as the sensor of the spectroscopic measurement system 16. This choice was based on the ease of directly addressing individual pixels in the array, and the opportunity for changing the integration time per pixel for more sensitive analysis. FIG. 1 and FIGS. 2a and 2b show the geometry of the illustrated embodiment used for spectroscopic measurements. The light source was a 588 nm AlInGaP light emitting diode 10 placed above the flow channels 14, which in turn were directly placed on the image array 12. Since the typical size of an elastomer microfluidic channel 14 is on the order of 50 to 250 microns wide by 10 to 20 microns deep, the absorption path length is quite small compared to more conventional cuvette-based absorption spectrometers with interaction lengths 100-1000 times larger.

According to the Beer-Lambert law, the absorbance A, is proportional to the concentration of the absorbing material c and the absorption path length l, so that:

$$A = \epsilon c l \qquad 1.1$$

where $\epsilon$ is the dielectric constant of the material, and c is the molar absorption constant or molar absorptivity. Thus, the difference in the expected detected intensity of a channel filled with reagent versus a channel filled with water is very small for dilute solutions. Therefore the higher the sensitivity of the detectors in the sensor array 12, the greater the concentration range that can be detected.

The first absorption experiment was performed using a ten-bit resolution black and white CMOS imager array 12 provided by NASA's Jet Propulsion Laboratory. This imager array 12 has a typical pixel size of 12 μm, a dynamic range >65 dB, and a responsivity >1.3 pV/photon at room temperature. The active imaging area consisted of 512×512 pixels. First, the minimum concentration of dye, which can be detected in this system, was determined. The absorptivity of various concentrations of bromophenol blue (Aldrich Chemical Company, Inc. #61425-28-9) were then tested on a calibrated Shimadzu BioSpec 1601 spectrophotometer with solution filled into 1 cm cuvettes. The molar absorption constant c was then calculated and a curve fit was applied to generate the control data for a 14 μm channel.

Next, a polydimethylsiloxane (PDMS) microfluidic chip 18 comprised of eleven 100 μm wide by 14 μm deep channels 14 spaced 100 μm apart was placed directly on our CMOS imaging chip 12. The channels 14 were filled with each concentration of interest and one channel 14 was filled with water for background measurements.

Figure 3A:
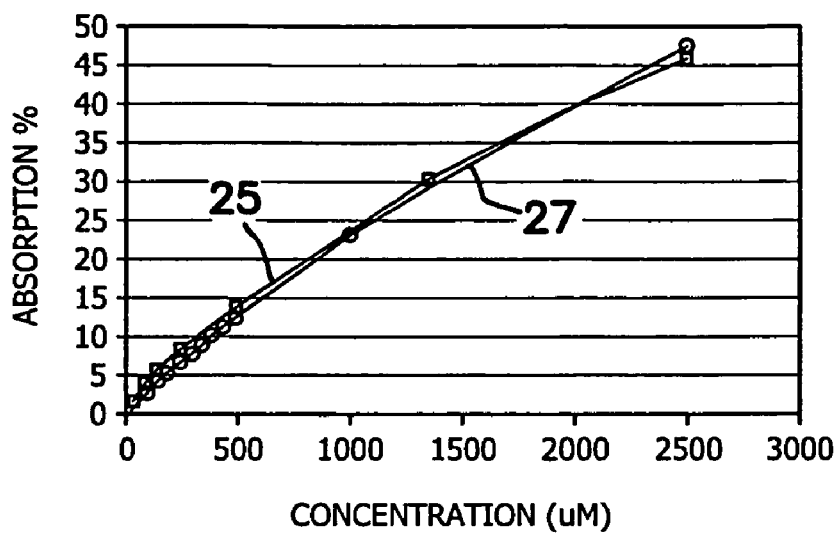
FIG. 3a and FIG. 3(b) are graphs of the absorption spectra of various Bromophenol Blue and Orange G concentrations respectively taken with a Shimadzu spectrophotometer as the control group and the APS CMOS imager of the invention.

FIG. 2b shows a typical image of light transmission through the multi-channel silicone structure 20 as observed by the CMOS imager array 12. The illumination source comprised a yellow AlInGaP LED 10 with $\lambda_{max}$=588 nm and $I_o$=1500 mcd, and was optimized for the absorption peak of bromophenol blue. Although it may be difficult for the human eye to distinguish the difference in the lower concentrations, the imager array 12 is more sensitive and can readily distinguish differences down to the sub-micromolar ranges. The results of the experiment are summarized in FIG. 3a. The CMOS imager data is shown by the lighter line 25, while the control group data is shown in the darker line 27.

Figure 3B:
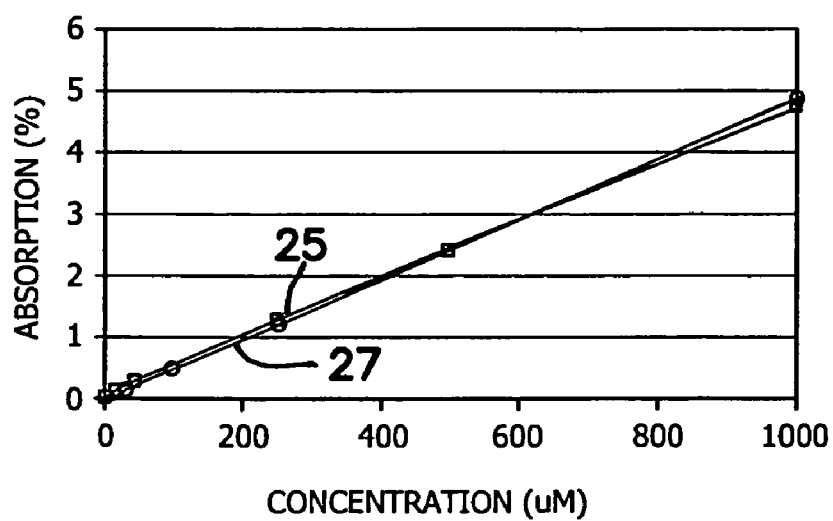

A similar test was conducted on Orange G, excited with light at 470 nm. Measurements were made by averaging the values from 5 mm long sections of the flow channel 14. The results of the experiment are summarized in FIG. 3b. The CMOS imager data is shown by the lighter line 25, while the control group data is shown in the darker line 27. Each of these sections has an approximate volume of 7 nL. Since the CMOS imager 12 allows for individual sections to be analyzed, any area which might have imperfections such as air or droplet formations could be selectively removed. From FIGS. 3a and 3b, it is seen that the monolithic CMOS device has a performance similar to a commercial Shimadzu spectrometer system over the conditions tested.

The important advantages of the imager spectrometers 16 over more conventional absorption spectroscopy systems include the capability to characterize spectra from picoliter volumes, and enable the observation of many channels 14 in parallel.

Broadband Absorption Spectroscopy

Figure 4:
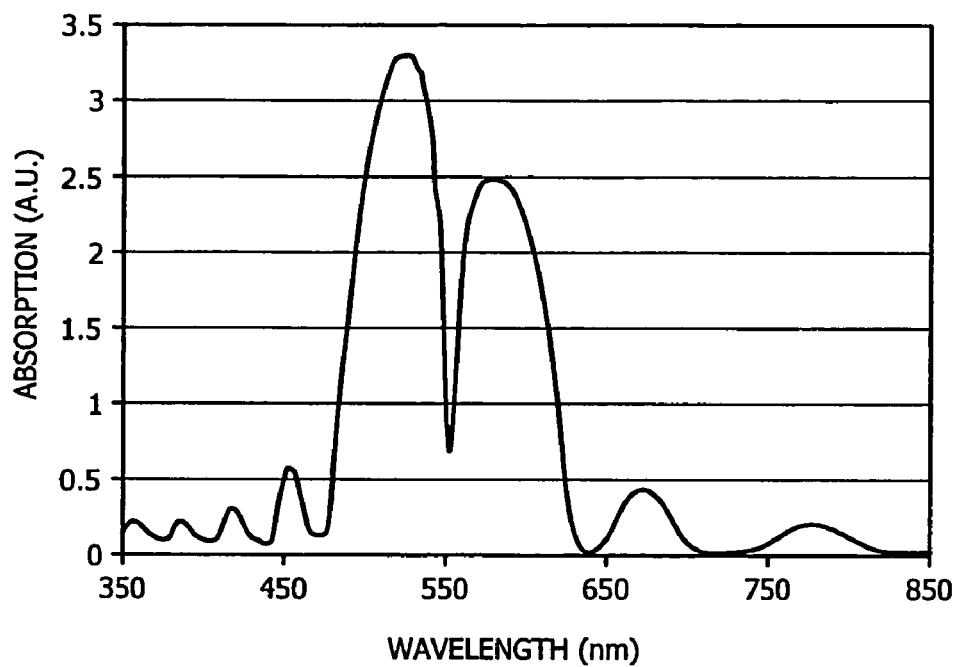
FIG. 4 is a graph of the absorption spectra of a 31 layer $SiO_2/Si_3N_4$ Fabry-Perot cavity.

A technique was described above in which the solution under test was known. This allows one to select the appropriate light source to best overlap with the absorption spectra and determine the concentration of the solution. However, in many cases, the solution under test is not known and broadband absorption spectroscopy is needed to determine the absorption spectra of the solution. For this application, individual detectors can be filtered by using $SiO_2/Si_3N_4$ multilayer Fabry-Perot cavity 23 shown in FIG. 1 with the absorption performance of a 31 layer Fabry-Perot cavity 23 shown in FIG. 4, which cavity 23 is deposited onto the silicon detector array 12 before definition of the fluidic structures on array 12. Filters 22 can be deposited with a deliberate thickness variation in order to obtain a specific wavelength response for each detector in the imaging array 12, providing a hyper-spectral imaging array. By pumping the solution of interest through flow channels 14 over these filtered detectors and observing their response, a spectrum of the absorption or fluorescence of a very small solution volume can be obtained.

Variable Filters

Dielectric thin film filters have been in use for the past several decades for a multitude of applications. They offer excellent reflectivity with minimum absorption over most wavelengths of interest. However, in their simplest form, which consists of a series of alternating $\lambda/4$ layers, they suffer from small reflectance bands and large side lobes. These problems can be corrected through material selection and careful design.

Another way to solve these problems is by stacking consecutive filters on top of one another. Although this approach might seem straightforward, in reality it requires very specific design criteria. In general, multilayer dielectric stacks are modeled before they are fabricated and in most cases they are generated for a single wavelength. In order for multiple wavelength filters to be grown on a single substrate, the thickness of the dielectric layers must be changed over the surface of the substrate. This can be accomplished in several ways, but typically involves changing the position of the substrate with respect to the source. A simple change in position can drastically affect the thickness of the deposition. Through this method, a geometrically graded multiple wavelength filter can be fabricated.

In most thin-film deposition, the consistency of the film is of critical importance. The film layers need to be homogeneous in thickness, purity, and index of refraction. Although one should be very concerned about the purity, and index of refraction, one can purposely take advantage of inhomogeneity in the thickness. The goal is to vary the thickness of the individual layers across the substrate, which allows for multiple wavelength filters to be fabricated on a single substrate. However, this must be done with a very precise method so that the wavelength range can be tailored to meet the specific application.

In order to understand how this can be accomplished, a quick review of magnetron sputtering physics is in order. A sputter system bombards ionized atoms into a specific target, which in turn knocks atoms off of the target. In reactive sputter systems, this is accomplished by providing a high-frequency AC field (typically 13.56 MHz) between the anode and cathode of the sputter source. This field ionizes atoms, typically an inert gas such as argon, which are used to expel atoms from the surface of the target. An inert gas is used so that no stochiometric reactions occur between the impinging species and the species that is sputtered. The sputtered target atoms follow the magnet flux lines generated by two permanent magnets contained within the magnetron sputter source. To generate other materials, such as $SiO_2$ from a Si target, another gas, i.e. oxygen, can be introduced into the system. As long as the necessary stochiometry conditions are met, the composite material will be grown.

The most straightforward method of varying the thickness of a film layer is by changing its position with reference to the sputter source. Since the probability of a sputtered atom impinging on the sample substrate is a function of its mean free path, by changing the geometric distance between the sample and the source, the thickness of the film layer can be changed. One is also able to predict the mean free path since it is a function of the system pressure and atomic diameter. With this knowledge a fairly accurate control of the sputtered layer thickness can be determined. The mean free path, mfp, can be predicted as follows $$mfp = \frac{k_g T}{\sqrt{2}\, p\pi d^2}$$

where p is the vacuum pressure, d is the diameter of the atom, $k_B$ is Boltzman's constant, and T is the temperature. Since the system uses RF sputtering, the system pressure can be lower and thus the fewer collisions will take place. This allows for a more line-of-sight sputtering to occur than in a DC system, which in turn enables the geometric grading of the sample. For example, the mean free path for Si at a pressure of 3 mTorr and room temperature is approximately 2.13 cm, which is more than enough to ensure that the sample will be coated. In reactive sputtering, the chemical reaction takes place on the substrate, thus allowing $SiO_2$ or $Si_3N_4$ to be grown. Since RF sputtering is a basically a line of sight process, the point of the sample closest to the target will have the thickest film deposition and likewise the farthest point from the target will have the thinnest deposition.

Before any fabrication occurs, the appropriate filter is modeled and its spectral response is calculated to ensure that the filter will behave as expected. Although modeling is not necessary for the simplest of filters, it is very necessary for producing filters with multiple extraction wavelengths or side lobe suppression. In general, multilayer dielectric filters can be modeled by an admittance matrix theory. Each layer has an admittance matrix which describes its behavior. These matrices can then be multiplied together to yield the overall system matrix. The model will not be derived, but the solution stated in matrix form as:

$$\begin{bmatrix} E_a \\ H_a \end{bmatrix} = \begin{bmatrix} \cos\delta & (i\sin\delta)/\eta_1 \\ i\eta_1\sin\delta & \cos\delta \end{bmatrix} \begin{bmatrix} E_b \\ H_b \end{bmatrix}$$

Where the upper and lower boundaries of the film-to-air interface are denoted by the a and b subscripts and E and H are the electric and magnetic field strengths of the light. $\delta$ is a factor used to correct for the phase change of the light wave travels through the medium of the film and is defined as:

$$\delta = \frac{2\pi N_1 \cos\varphi_1}{\lambda}$$

Where $\phi_1$ is the angle of refraction of the light beam in the film and $N_1$ the complex index of refraction of the film. $\eta_1$ is the optical admittance at oblique incidence in the film, namely $H_1/E_1$, and similarly for $\eta_r$ and $\eta_m$ below, where r designates the reflection beam, and m the substrate or emergent medium.

An assembly of thin films q in number can then be characterized by applying the above method as follows.

$$\begin{bmatrix} B \\ C \end{bmatrix} = \left\{ \prod_{r=1}^{q} \begin{bmatrix} \cos\delta_r & (i\sin\delta_r)/\eta_r \\ i\eta_r\sin\delta_r & \cos\delta_r \end{bmatrix} \right\} \begin{bmatrix} 1 \\ \eta_m \end{bmatrix}$$

The reflectance, R, transmittance, T, and absorptance, A, can now be calculated where the following relationship must hold $$1 = R + T + A$$

$$R = \left(\frac{\eta_0 B - C}{\eta_0 B + C}\right)\left(\frac{\eta_0 B - C}{\eta_0 B + C}\right)^*$$

$$T = \frac{4\eta_0 \mathrm{Re}(\eta_m)}{(\eta_0 B + C)(\eta_0 B + C)^*}$$

$$A = \frac{4\eta_0 \mathrm{Re}(BC^* - \eta_m)}{(\eta_0 B + C)(\eta_0 B + C)^*}$$

At this time it is also useful to define Absorbance which is an easily measured quantity as $$\mathrm{Abs} = \log_{10}\left(\frac{1}{T}\right)$$

Figure 5A:
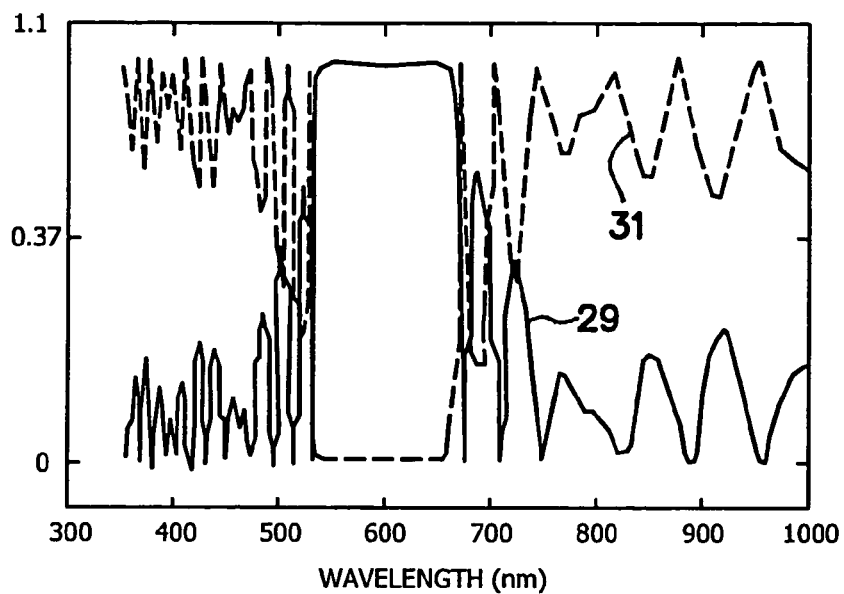
FIGS. 5a and 5b are calculated spectra for both a high reflectivity filter and a half-wave cavity respectively. The reflectivity of the filter and quality of the cavity are both functions of the number of dielectric thin-film layers and the index of refraction of the material. The materials modeled were $SiO_2$ and $Si_3N_4$.
Figure 5B:
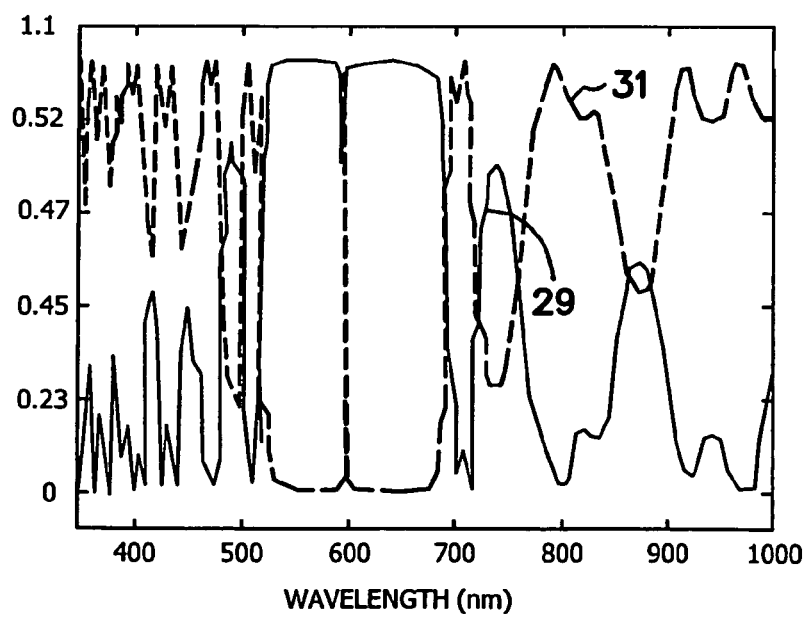

The calculated spectrum for both a high reflectivity filter and a half-wave cavity are shown in the graphs of FIGS. 5a and 5b. The solid line 29 is the reflectivity percentage as a function of wavelength and the dotted line 31 is the transmission percentage as a function of wavelength. The reflectivity of the filter 22 and quality of the cavity 23 are both functions of the number of dielectric thin-film layers and the index of refraction of the material. For the spectrums in FIGS. 5a and 5b, the materials modeled were $SiO_2$ and $Si_3N_4$ in a 31 layer $\lambda/4$ dielectric thin film reflector and in a 31 layer $\lambda/4$ dielectric thin film half wave cavity respectively.

The thin-film filters were grown using a toroidal magnetron source reactive sputter deposition system. The source has a two inch 99.999% purity Silicon target. The $SiO_2$ and $Si_3N_4$ films are grown by a stochiometric process in which $O_2$ or $N_2$ are admitted into the system, respectively. The initial plasma is started by flowing Ar into the system and increasing the pressure to 30 mTorr. After a plasma has ignited, another process gas is admitted into the system and the system pressure is regulated to 3 mTorr. The system is computer controlled and the deposition rate and film thickness are measured by a crystal monitor.

Before the actual filters were grown, the system was calibrated by growing single layer $SiO_2$ and $Si_3N_4$ films respectively on silicon substrates. These films were then patterned through photolithography and etched in a reactive ion etcher (RIE) so that the film thickness could be measured with an Alphastep 500 surface profilometer. After the thickness had been measured, each sample was placed onto a Focus ellipsometer to measure the refractive index, n, and extinction coefficient, k, of the material. For $SiO_2$, n=1.47 and k=0.00001. For $Si_3N_4$, n=2.05 and k=0.00001. These values indicate that the films are of high quality.

The actual filters are fabricated on glass coverslips, which have been precleaned prior to deposition. The filters consist of 23 to 41 total layers depending upon the desired reflectivity.

For a 23 layer structure, the first 11 layers comprise of alternating layers of $Si_3N_4$ and $SiO_2$, which are $\lambda/4$ thickness. This is then followed by a $\lambda/2$ thick layer of $SiO_2$. The filter is completed by growing 11 more, $\lambda/4$ thick, alternating layers of $Si_3N_4$ and $SiO_2$. This procedure produces a Fabry-Perot cavity structure which only passes a very narrow band of incident light. Due to system limitations, only one substrate can be processed at a time; however, due to the precision control of the deposition system, reproducibility is very high.

Once the appropriate wavelength has been chosen for the notch filter, a recipe is generated which includes the appropriate layer thickness and gas mixture. The recipe is easily generated via a software program that was built into the deposition system control software. After loading the sample, it must be placed in proper position to allow for the geometric grading to occur. The sample stage has X, Y, Z translation and rotation capability, which allows for precise placement of the sample.

Figure 6A:
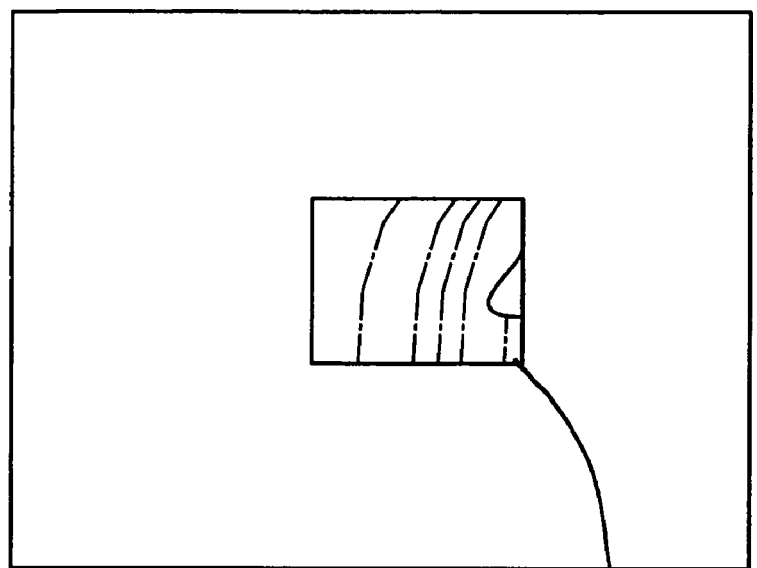
FIG. 6a is a photograph of a geometrically graded filter grown in a reactive sputter deposition system to produce a planar rainbow bar filtration pattern which can be oriented orthogonally to the flow channels for spectroscopic use. The grading is produced by placing the sample at an angle to the sputter source.
Figure 6B:
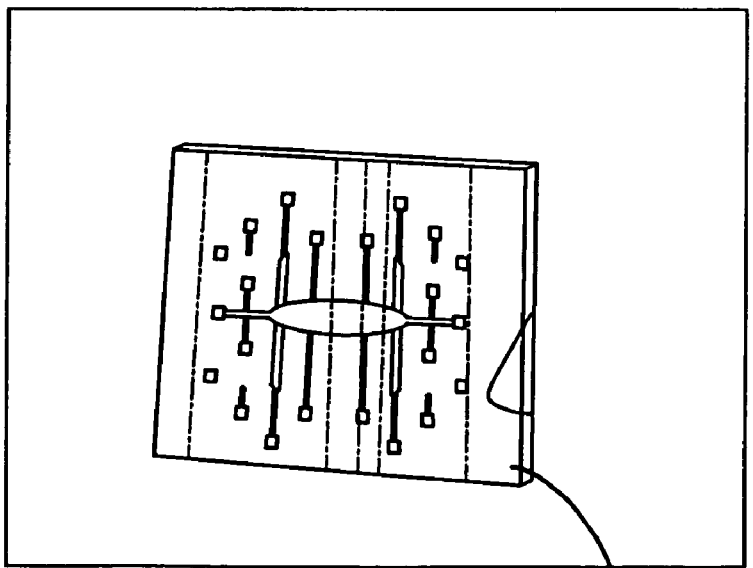
In FIG. 6b is a photograph of a patterned or geometrically graded filter with flow substrate sealed to the surface of the filter with the flow channels running across the gradation of the filter.

A photograph of the filter is shown in FIGS. 6a and 6b. FIG. 6a is a photograph of a geometrically graded filter 22 grown on a reactive sputter deposition system. The grading is produced by placing the filter at an angle to the sputter source. FIG. 6b is the patterned filter 22 of FIG. 6a with a flow substrate 15 sealed to the surface of filter 22. After the filter 22 is grown, it is then patterned via photolithography to produce a 20 µm by 20 µm grid on the surface of the filter 22 to put an opaque frame around each pixel to provide planarity and isolation of one pixel from another.

Figure 7:
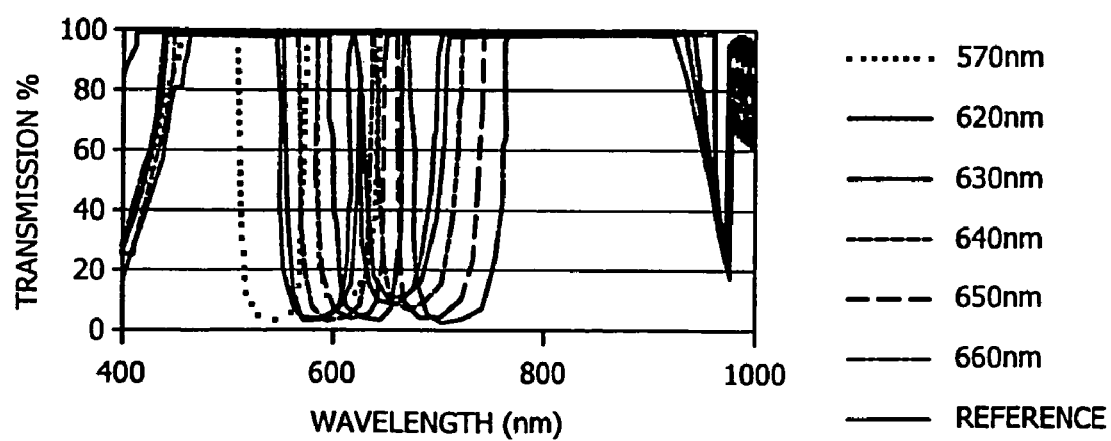
FIG. 7 is a transmission spectrum of the graded filter of FIG. 6a showing the maximum and minimum wavelength filter responses.

The filter 22 was tested via an Ocean Optics Fiber optic spectrometer so that the individual filter elements could be tested. FIG. 7 is a graph which illustrates the measured spectrums which were of primary interest for testing at six different positions on the graded filter 22. The transmission percentage of six graded filters 22 are graphed with a reference and show a complex pattern of overlapping transmission spectra in which transmission minimums increase with increasing lateral position along the gradient of the graded filter. This particular filter was designed to operate between 450 nm and 750 nm thus providing coverage for most of the visible wavelength range. It should be noted that these filters are not intended to work with white light sources. Multiple blocking filters would have to be added to the assembly in order to produce an adequate extraction from white light; however, this is possible using the same techniques described above.

Figure 8:
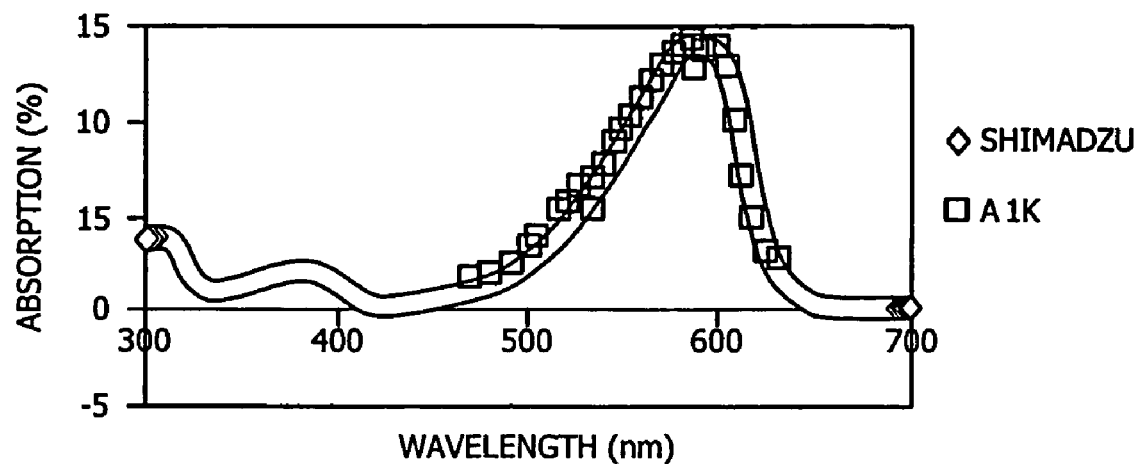
FIG. 8 is a graph of the spectrum of bromophenol blue taken by the CMOS imager with graded filter of the invention and as taken by a Shimadzu 1601 spectrophotometer.

FIG. 8 presents a graph of a spectrum using the graded filter system and a reference spectrum taken with a Shimadzu 1601 spectrophotometer. The spectrum was obtained by illuminating the microfluidic system with a series of commercial LED'S and applying signal processing (discussed below) to the acquired images. Since each filter wavelength is known, and the position of each filter element with reference is known, a spectra can be generated. It should be noted that the system relies on the fact that the contents of the microfluidic channel are uniform throughout its volume. As can be seen from FIG. 9, our system offers comparable performance to the commercial system.

Fluorescence Spectroscopy

During fluorescence spectroscopy, the sample under test is excited with a light source 10 whose wavelength is close, within 10 to 50 nm, to the emitted fluorescent light. Typically the light pump source is much brighter than the fluorescence signal, especially for experiments involving small numbers of fluorescing dye molecules, such as when performing single cell detection. Without a very efficient filter, the pump beam saturates the imager 12, precluding any chance of identifying the fluorescent signal. A blocking filter, which is tuned to the pump wavelength, must be placed between the microfluidic device 18 and the imager 12, and should be transparent at the fluorescent wavelength.

Figure 9:
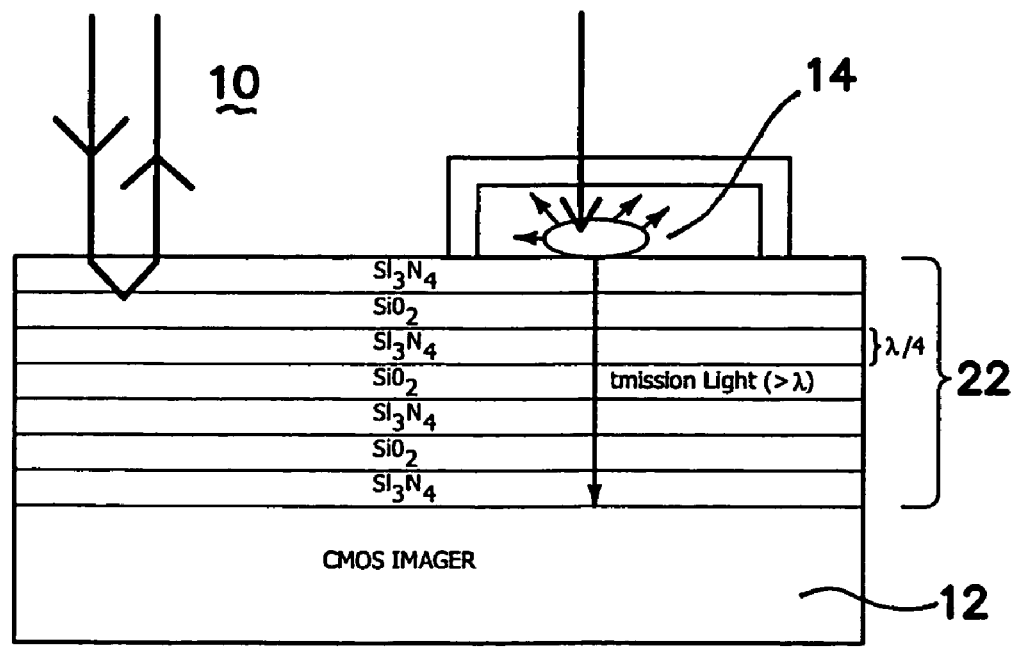
FIG. 9 is a side cross-sectional view of a diagram of a quarter wavelength dielectric thin-film filter grown on the CMOS imager of the invention to block the excitation light, but pass, with minimal loss, the emission Light.

The filter 22 can easily be fabricated as a carefully grown dielectric thin-film mirror as shown in FIG. 9. A typical filter 22, deposited by reactive sputter deposition of alternating $\lambda/4$ layers of silicon dioxide and silicon nitride, is transparent at the fluorescent wavelength, and blocks over 99% of the incident pump wavelength.

Figure 10:
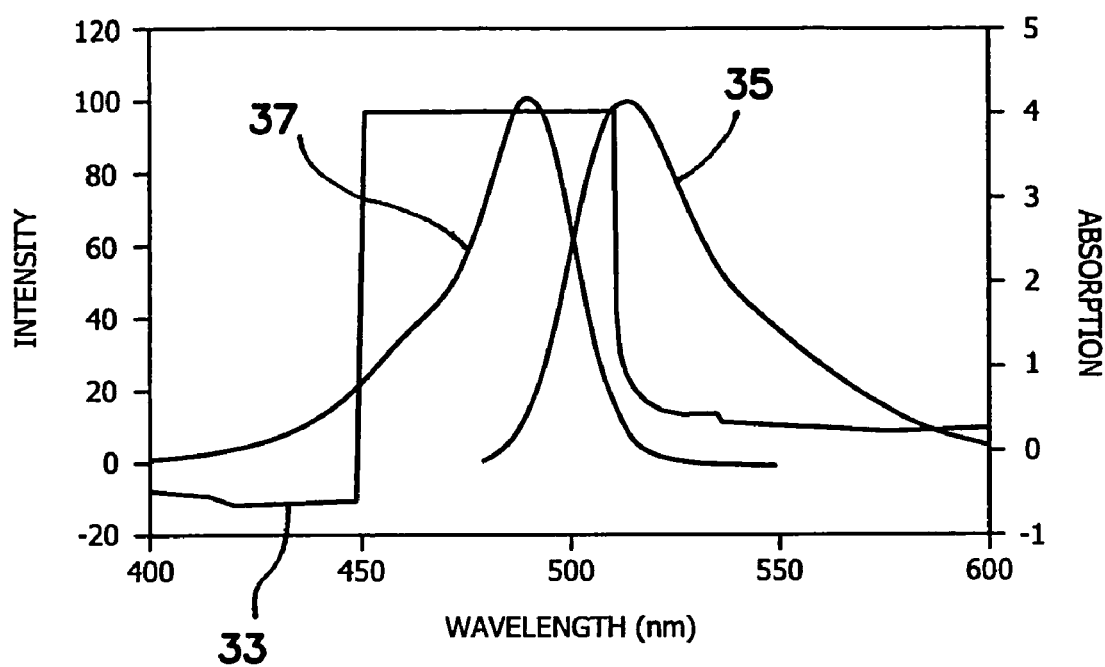
FIG. 10 is a graph of the fluorescent absorption and emission spectra for fluorescein. The blocking filter absorption spectrum shown in relation to second y axis. The emission peak corresponds to a region just outside the block band where the transmission is roughly 50%. This can easily be improved by constructing a narrower bandblocking filter.

Diluted fluorescein dye was used to test the performance of our monolithic fluorescence system. FIG. 10 is a graph which shows the absorption and emission spectra of the fluorescein dye, together with the reflectivity spectrum of the dielectric blocking mirror. Since the mirrors and flow channel are directly deposited onto the silicon CMOS detector array 12, we can use the lensless contact image from this array to differentiate between concentrations of fluorescein.

Spectrally resolved fluorescence measurements are also possible by slowly varying the spectral position of the reflectivity edge of the dielectric blocking minor and measuring fluorescence intensities in different sensor pixels protected with filters with different reflectivity edges. The requirement for obtaining a high-quality fluorescence image on a miniaturized chip-based spectrometer relies on very efficient blocking of the incident excitation light by the filter 22 whose absorption spectrum is shown in the graph of FIG. 10 as a function of wavelength. Otherwise the excitation light would overwhelm the fluorescing signal. Line 33 is the spectrum of the blocking filter, line 37 the fluorescein absorption and line 35 the fluorescein emission intensity.

Figure 11:
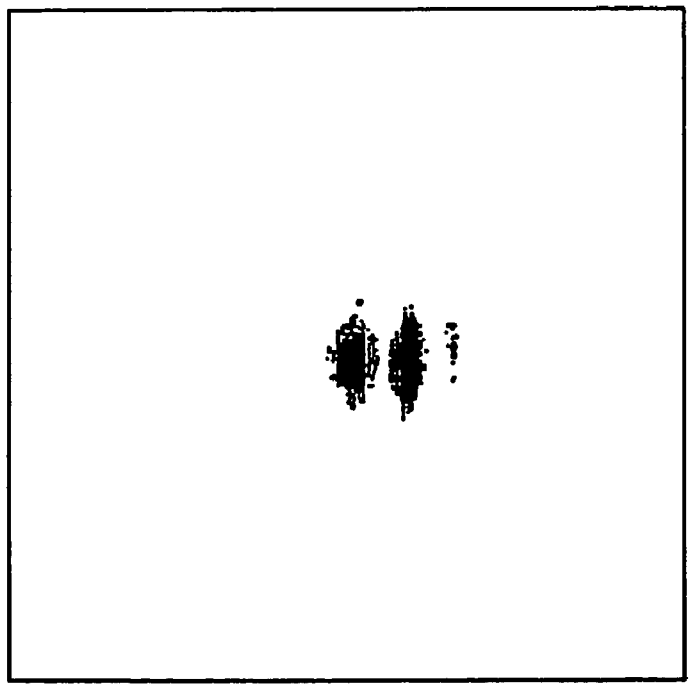
FIG. 11 is a microphotograph of a 170 μM and 85 μM fluorescein in 100 μm wide by 14 μm flow channels on 460 nm blocking filter illuminated by an Ar ion laser at 488 nm with no. 2 and no. 5 neutral density filters In the beam path to decrease the excitation light intensity so that the Imager is not saturated.

FIG. 11 depicts a sample image acquired with the system. In the image of FIG. 11, two channels were filled with different concentrations of fluorescein and illuminated with laser light. The channels were 100 µm wide and spaced 100 µm apart. The channel that resides in between the two test channels was filled with water for reference purposes. The image illustrates that virtually all of the excitation light was blocked, and only fluorescence light was acquired by the imager. As stated previously, the reader may find it difficult to distinguish a difference between the two channels due to the loss of resolution in conversion of the imager data to picture format; however, the imager 12 is capable of making the distinction. In fact, the concentrations of fluorescein shown in FIG. 11 locally saturate the imager 12.

Although the CMOS imager is very useful for performing spectroscopy, the results shown previously are not trivial to obtain. The imager 12 transmits information as an analog voltage which is then digitized by an analog to digital converter (ADC.) The imager 12 does have the ability to transmit a digital data stream which provides a simpler retrieval method. However, the digital data stream is limited to 10 bit resolution which limits the achievable detection limits of the system. By using the analog mode, a full 13 bits of information is achievable and this is only limited by the DAC card installed in the capture system. The data is collected by using conventionally programmed Labview software and is saved to an ASCII text file. This data can then be imported into Matlab and analyzed.

For a typical graded filter absorption experiment the light source 10 is measured with a spectrometer to obtain its spectrum. This spectrum is then used to spectrally normalize the data obtained during the experiment using a digital data processor or signal processor. Once the image is acquired, the data is manipulated so that each of the corresponding wavelengths can be obtained by geometrically normalizing the pump light to the filter characteristics. Then each specific wavelength/area is interpreted by comparing the solution under test to the specific solvent reference channel.

For other applications it is necessary to convert the data files into a bitmap image. A program was written to convert data files to both 8 bit and 16 bit bitmaps. The program was written especially so that large batches of files could be converted simultaneously since it is very easy to obtain a number of data files during a single experiment. The program is very useful for applications which have a large amount of data files that could be viewed as bitmaps.

Cell Sorting

One of the most practical applications for fluorescence spectroscopy is flow cytometry and furthermore fluorescence activated cell sorting (FACS.) By using the process described above, these applications can be performed with very similar results to current standard techniques. Cell sorting in microfluidic channels was has been previously performed, although the cell sorting was done inside a flow channel, and the optical detection system involved a laser, photomultiplier tube, and the appropriate filters. The detection system was far from miniaturized. Cell sorting was successfully accomplished with the integrated system described above.

Figure 12A:
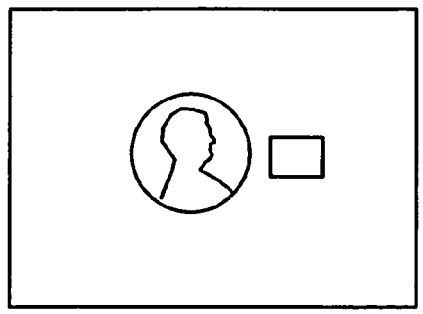
FIG. 12a is a photograph of a cell sorting chip as compared to a penny.
Figure 12B:
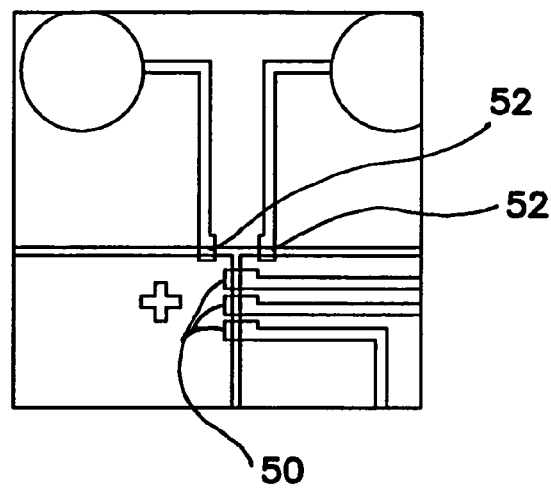
FIG. 12b is an enlarged image of a portion of the cell sorter chip taken with the integrated imaging system showing the T channel, pump, and valves.

In order to perform μFACS, a suitable flow cell had to be fabricated. The flow cell comprised of a T channel in which a narrowing occurred just before the T. The nominal channel width is 50 μm which then narrows to approximately 10 μm. A microphotograph of the cell sorter chip 24 is shown in FIGS. 12a and 12b. The sorting is performed by integrating valves 50 and a pump 52 through conventional soft molding techniques. The system is computer controlled through Labview which acquires a signal from the imager 12 and tells a microcontroller to open or close the appropriate valves. Eventually, one could eliminate the PC control by hardwiring the microcontroller and imager together, thus simplifying the system even more. For further miniaturization the Labview computer could be replaced with a digital signal processing (DSP) chip which would allow for a compact electronics package capable of performing both absorption and fluorescence based sorting.

The system was tested by using 10 μm diameter fluorescently labeled beads. The beads were loaded into the channel in an aqueous buffer in very low concentration, so that statistically only one bead is interrogated at a time. A commercial LED (Stanley LED), with a peak wavelength of 505 nm, was used for illumination of the sample and a multilayer interference filter was used to extract the appropriate pump wavelength while blocking the remaining light. Another interference filter was placed on the imager 12 to allow the fluorescence to pass while blocking any stray pump light. As a bead passed within the interrogation region, the imager signal was analyzed to determine whether it was fluorescent or not and then the appropriate sorting command was sent to the microcontroller. After the beads had been sorted a fluorescent measurement of the two sorting chambers was made to show how accurate the sorting was. The data for the experiment is presented in Table 1 below. The sorting rate and accuracy for the first trial was relatively low, so tighter tolerances were established for the sort criteria. This improved the sorting accuracy, but unfortunately the sorting rate remained between two and three beads per second. The performance of the system could be improved by maximizing the signal-to-noise ratio of the imager 12. This is highly dependent upon the extraction and blocking filter performance as well as the intensity of the LED.

TABLE 1

Table 1. Sorting accuracy for the integrated μFACS.

| Trial | Time(s) | Beads Sorted | Beads Missed |
| --- | --- | --- | --- |
| 1 | 120 | ≅70 | 13 |
| 2 | 300 | ≅150 | 19 |
| 3 | 600 | ≅275 | 26 |

The monolithic integration of the microfluidic device directly on an image sensor array 12 has been demonstrated above. The next component of the system, which must be miniaturized, is the light source. In a typical visible spectrophotometer the light source is generally a tungsten or tungsten-iodine filament lamp with some models also including light emitting diodes. In a miniature spectrometer, the appropriate light source depends heavily upon the application and heat dissipation problems. The most convenient alternatives include solid-state light emitting diodes, laser diodes, white light sources, and perhaps even the sun. For infrared analysis, the source might also be a tungsten filament lamp with a specific color filter placed directly over the microfluidic device.

Although for many applications, an array of vertical-cavity surface emitting lasers (VCSELs) could be desirable, such laser sources are very difficult to construct in the most interesting UV-visible wavelength range. Instead of using lasers, high finesse optical cavity filters can be defined on top of LED arrays to obtain filtered light sources, which can be directly placed on top of the microfluidic channel, which in turn is placed on top of a detector array, to create a fully functional on-chip visible spectrometer.

Vertical-Cavity System

Figure 13:
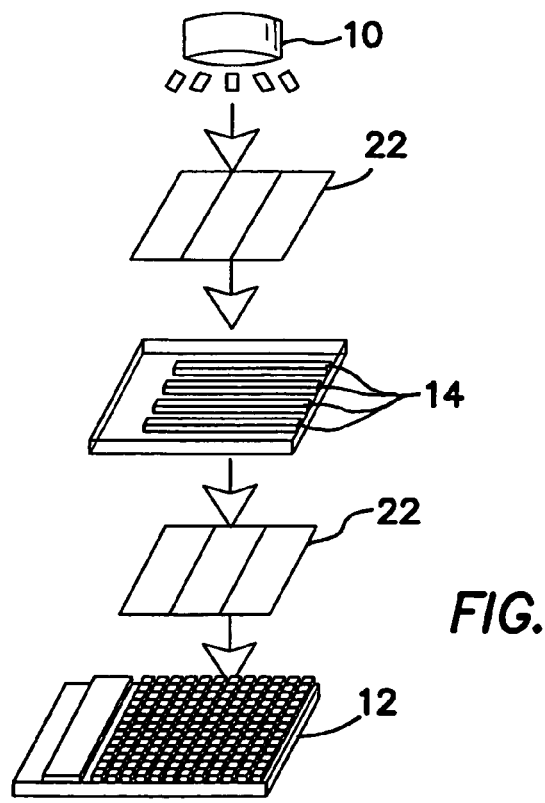
FIG. 13 is an exploded perspective view of a vertical-cavity based analysis system of the invention.

As previously shown, a fully integrated detection system can be created by placing the microfluidic channels 14 directly on a CMOS imager 12 with the appropriate thin-film filters 22 in place. Although the system previously discussed provides adequate sensitivity for most measurements, it is path length limited and its ultimate sensitivity could be improved. To this end, an integrated vertical-cavity system was developed to enhance the system sensitivity. A schematic illustration of this system is depicted in FIG. 13.

As described above, due to the Lambert-Beer law, absorption and therefore luminescence are path-length dependent. For most commercial spectrophotometers the path length is on the order of 1 cm. A typical microfluidic system has a channel height of 10 μm, which makes the absorption three orders or magnitude less than a commercial system. However, with the introduction of a vertical cavity structure the virtual path length can be much longer than the physical path length. This is due to the multiple passes of the light through the flow channel before exiting the cavity. However, several conditions must be met before the cavity will provide enhancement.

At this time a brief review of some of the basic concepts of cavity theory will be presented. The most straightforward cavity to analyze is the Fabry-Perot etalon. A Fabry-Perot etalon is formed by placing two reflectors a distance d apart around some medium. Each reflector has a certain reflectivity, i.e. $R_1$ and $R_2$. For the simplest case, one can assume $R_1=R_2=R$. As a wave enters the cavity, it undergoes a phase shift proportional to the separation distance d and the index of refraction of the media. This can be written as $$\delta = 2\pi nd \cos(\theta_i)$$

where δ is the phase change (radians), n is the index of refraction of the medium, d is the separation distance, and $\theta_i$ is the angle of the incident light. For resonance to occur, the phase shift for one round trip through the cavity has to be an integral multiple of n: and can be summarized as $$\delta_{1f} - \delta_{1r} = m\pi \quad m = 1, 2, 3 \ldots$$

A common figure of merit for a cavity is its quality factor, or Q. The Q of a cavity can defined as follows $$Q = \omega \frac{\text{Energy Stored}}{\text{Power Dissipated}}$$

where ω is the frequency (radians.) The Q of a cavity is also related to the full-width half power points as $$\Delta v_{\frac{1}{2}} = \frac{v}{Q} = \frac{c[\alpha - (1/d)\ln(\sqrt{R_1 R_2})]}{2\pi n}$$

where c is the speed of light, α is the distributed loss constant, and v is the cavity resonant frequency.

Admittance matrix theory is used to analyze the vertical cavity structure. This stems mainly from the fact that dielectric thin-film reflectors are being used in the structure and admittance matrix theory allows for straightforward modeling of the reflectors as noted above. Each layer in the structure can be described by a characteristic admittance matrix. Each of the matrices can then be multiplied together to determine the full characteristic matrix of the system.

The transmission, reflection, absorption, and Q of the cavity can all be calculated from this method. For example, if the reflectors are comprised of alternating λ/4 layers of high and low index materials, the reflectance of the mirror can be easily calculated by $$R = \left( \frac{1 - \left(\frac{n_h}{n_l}\right)^{2p} \left(\frac{n_h^2}{n_s}\right)}{1 + \left(\frac{n_h}{n_l}\right)^{2p} \left(\frac{n_h^2}{n_s}\right)} \right)^2$$

where $n_h$ and $n_l$ are the indices of refraction of the high and low index materials respectively, $n_s$, is the index of the substrate, and 2p+1 is the number of layers in the stack.

One of the problems encountered when using the admittance matrix approach for characterizing the cavity structure is that concentration does not appear anywhere in the admittance matrix model. To this end, the concentration of the material inside the flow channel has to be related to the extinction coefficient k that a light wave sees as it passes through the material. This relationship can be determined by noting that the absorption is proportional to the irradiance of the light by $$A = \log\left(\frac{I_0}{I}\right)$$

where $I_o$ is the incident irradiance and I is the irradiance of the light after it passes through the material. In electromagnetic terms, the irradiance of the light can be written as $$I = \frac{1}{2} nY |E^2| e^{\frac{-4\pi k}{\lambda}(\alpha x + \beta y + \gamma z)}$$

where E is the electric field amplitude, Y is the admittance of free space, λ is the wavelength, and α, β, γ are the direction cosines. (Note: direction cosine α is not to be confused with the distributed loss coefficient.) Since we are only interested in light propagation in the z direction, the equation simplifies. The points of interest are at z=0, and z=d, the incident irradiance and the irradiance after passing through the material, respectively. It can be shown that;

$$A = \log\left(e^{\frac{4\pi k d}{\lambda}}\right)$$

Now, by substituting for A and solving for k, one can determine the necessary correlation between concentration and extinction coefficient as follows $$k = \left(\frac{\ln(10)}{4\pi}\right) \lambda \varepsilon c \cong .1823 \lambda \varepsilon c.$$

As stated previously, the admittance matrix method was used to model the physical structure. Each reflector and the flow structure have characteristic matrices associated with them. These matrices were calculated based on several variable parameters, such as flow channel height, sealing membrane thickness, concentration, and total separation distance between the reflectors. A computer model was generated to find the optimum value for these parameters.

In order to accurately model the device, it was necessary to include a suitable model for the flow channel. Although the model determines the optimized value for channel height and membrane thickness, the model must include the solution of interest that will reside within the flow channel. To this end, water was used as the primary solution for index matching purposes. However, the extinction coefficient of water was modified to resemble a lossy dye such as bromophenol blue. The absorption loss was modeled as a Gaussian curve centered around 591 nm which is the absorption peak for bromophenol blue. The last equation above was used to relate the extinction coefficient to the molar absorptivity, wavelength, and concentration. Through this method a more accurate determination of the physical parameters was obtained. The simulation used an iterative method based upon initial dimensions which could be fabricated.

Figure 14:
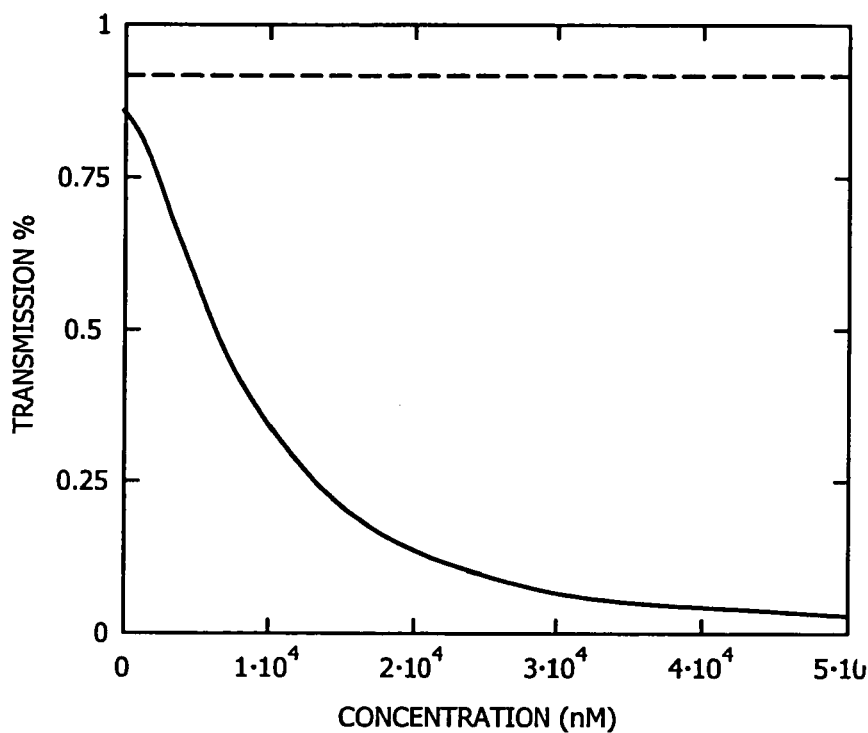
FIG. 14 is a graph of a simulation of the vertical cavity transmission (red) spectrum as a function of concentration at $\lambda$=591 nm. The flow structure without the cavity (blue) is shown for comparison.

Along with the cavity structure a simple flow channel structure based on the same parameters minus the reflectors was calculated. The simulation was performed with Mathcad 2001i. FIG. 14 is a graph which illustrates the transmission of the vertical cavity structure and the stand alone flow channel structure as a function of concentration. As can be seen, the vertical cavity structure provides great enhancement over the standalone flow structure.

Figure 15:
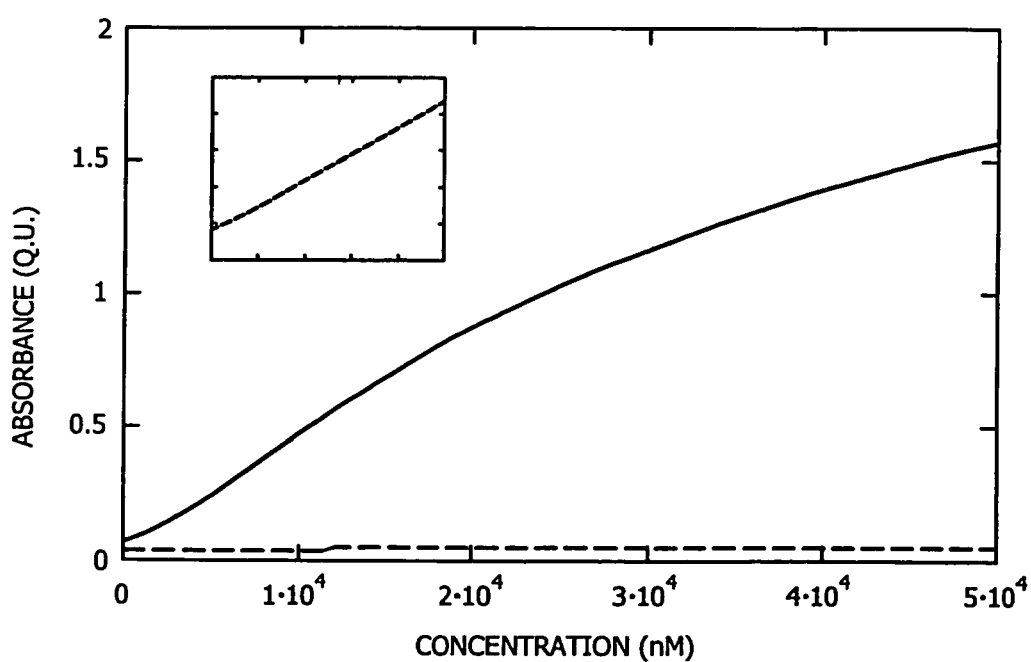
FIG. 15 is a graph of the absorbance of the vertical cavity structure shown in solid line verses the noncavity structure shown in dotted line. The inset of FIG. 15 shows that the noncavity absorbance is linear as expected.

Although transmission is an excellent measure of enhancement, it is often more acceptable to examine the absorbance as a function of concentration. Absorbance as described earlier is standard for performing absorption spectroscopy and for noncavity structures is linearly proportional to the concentration. This can be seen from the graph of FIG. 15. The cavity provides enhancement and thus is nonlinear with concentration.

Figure 16:
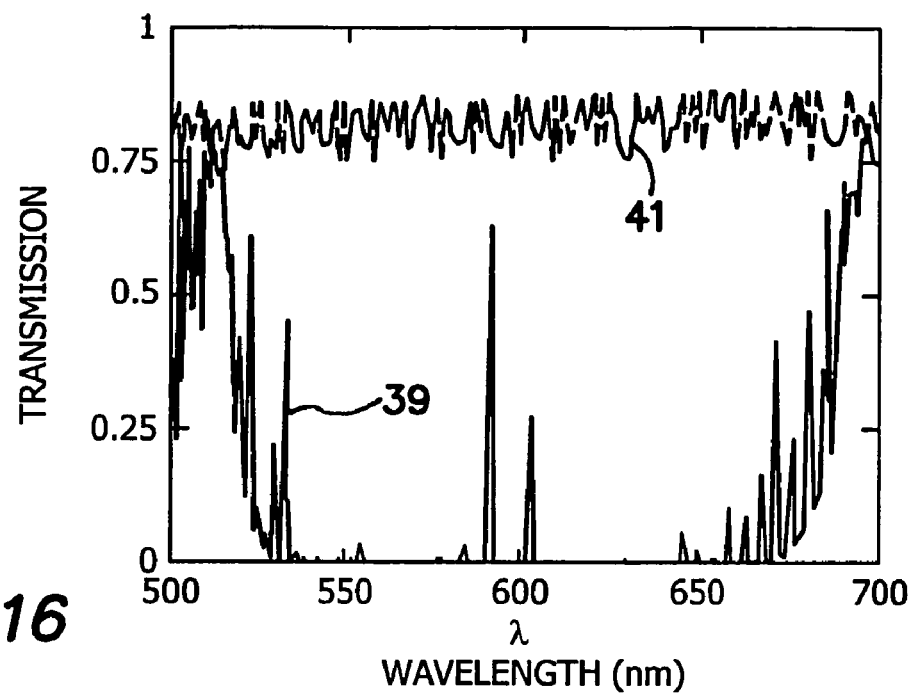
FIG. 16 is a graph of the simulation of the vertical cavity transmission (red) spectra vs. the same flow structure without a cavity (blue). The cavity is designed to operate at $\lambda$=591 nm.

The cavity's wavelength dependence is illustrated in the FIG. 16. The transmission spectrum of the vertical cavity 23 is shown by line 39 as compared to the spectrum of the same flow structure without a cavity as shown by line 41. A design wavelength for the cavity of λ=591 nm was chosen to overlap with the peak absorption wavelength of bromophenol blue which was used to test the device. In addition to the peak at 591 nm another peak at a slightly longer wavelength can also be seen. This is due to the multimode nature of the cavity. The reflector separation distance is large enough to support multiple cavity modes. The enhancement of the cavity can also be calculated and optimized from the model. One can determine the enhancement for the 591 nm mode from FIG. 14 and can reach a predicted maximum of 1000. The vertical cavity structure provides enhancement for low concentrations, but the enhancement saturates as the concentration increases above 100 µM.

Figure 17:
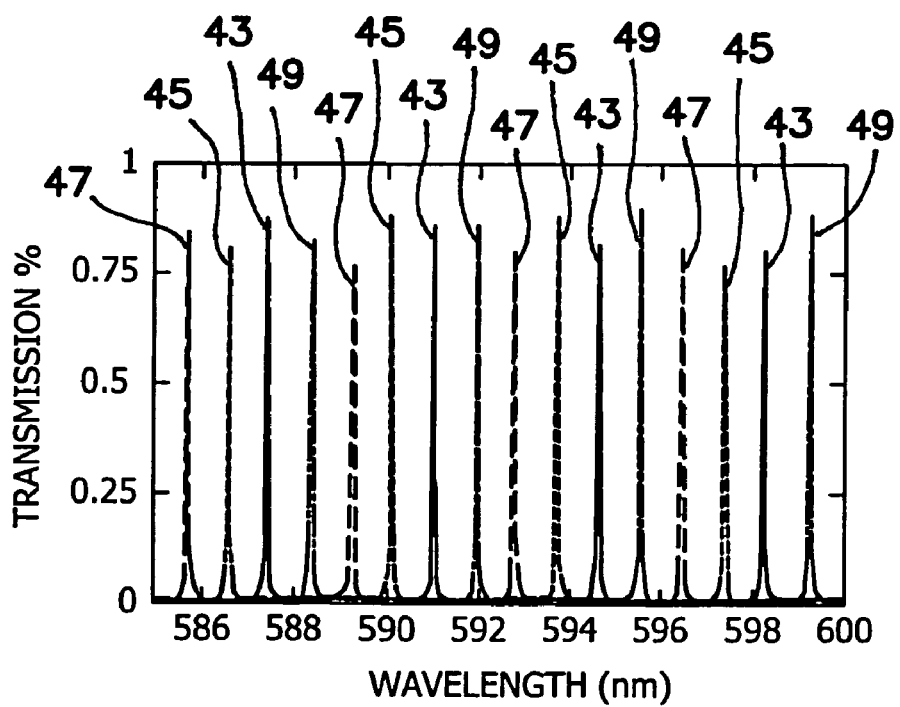
FIG. 17 is a graph showing the variable tuning of the vertical cavity structure as a function of separation distance.

The simulation was extended to look at the tunability of the cavity. Since the cavity reflectors are separated by an elastomeric flow structure, the cavity spacing can be changed slightly by pressurizing the flow channels. Due to the nature of the device, the flow channels cannot be deformed as much as in normal multilayer devices; however, a small expansion can cause a significant change in the phase matching condition of the cavity. The phase change is linearly proportional to the separation distance of the reflectors. This distance changes as the pressure inside the flow channel increases as controlled by external pumps (not shown) and the elastomer expands. Thus, the invention contemplates that the fluidic circuit may be provided with some flow channels or chambers which are solely dedicated to pressurizing the material of the fluidic circuit to change its thickness. Through this technique, the cavity can be tuned so that the cavity modes change. This is shown in FIG. 17 which illustrates the change in transmission peaks as a function of wavelength and change in separation distance. Transmission peaks 43 correspond to a nominal channel height, peaks 45 to a channel height increase of 1 µm, peaks 47 to a channel height increase of 2 µm, and peaks 49 to a channel height increase of 3 µm. The separation distance change was limited to 2 µm, since this is achievable with PDMS. Although the tuning is hard to control since the pressure resolution is fairly large, the technique could be useful to overcome some fabrication tolerances.

The device described above was fabricated by combining standard semiconductor fabrication and soft lithography. The reflectors are λ/4 dielectric thin-film stacks comprised of $SiO_2$ and $Si_3N_4$ which are deposited on No. 1 glass microslip covers. The thin-film stacks are deposited by reactive sputter deposition which allows for accurate thickness and low internal stress. The reactive sputter deposition system also allows for a geometric grading of the thin-film stacks so that multiple wavelength cavities can be grown on a single substrate. The reflectors typically have between 15 to 20 layers depending upon the desired reflectivity. For this application, the reflectance of the mirrors is between 92% and 98%.

Figure 18A:
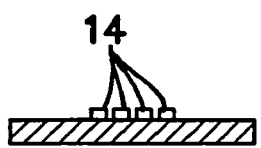
FIGS. 18a-18d is a sequence of diagrams illustrating the fabrication procedure for creating the vertical cavity structure of FIG. 13. Care must be given to the fabrication tolerances for success.
Figure 18B:
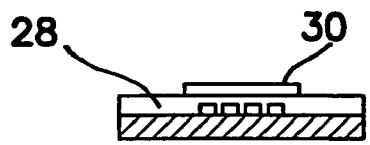
Figure 18C:
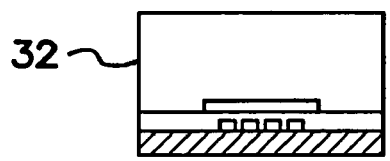
Figure 18D:
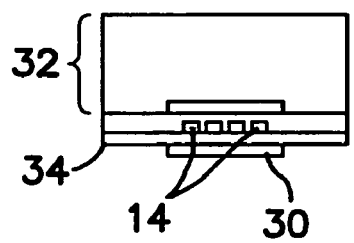

The microfluidic system is fabricated using multilayer soft lithography techniques as shown in FIGS. 18a-18d. A flow channel mold 14 is constructed using SU8-2015 spun at 4500 RPM for 45 seconds with a 480 RPM spread cycle for 6 seconds as shown in FIG. 18a. SU8 spinning was performed using a Laurel spinner model WS-400A-6NPPILITE. The mold height was measured with an Alphastep 500 profilometer and yielded a height of 12.60 µm. The flow channel structure was then formed by spinning 20:1 GE RTV615 PDMS at 2500 RPM for 60 seconds onto the mold as shown in FIG. 18b. This yields a flow structure 28 of 14.4 µm height. The flow structure 28 was cured for 15 minutes at 80° C. A sealing membrane was then formed by spinning 5:1 GE RTV615 PDMS at 5400 RPM for 60 seconds. RTV spinning was performed using a SCS Spincoater model 6700. The membrane thickness was measured to be 9.5 µm. The membrane was also cured for 45 minutes at 80° C. After curing the flow structure, the top reflector 30 was placed over the flow channels 14 and 30 g of 5:1 GE RTV615 PDMS was poured on top of the reflector-flow structure assembly as shown in FIG. 18c. This was then allowed to cure for 45 minutes at 80° C. After curing the flow system 32 was removed and placed on top of the sealing membrane 34 as shown in FIG. 18d. The entire assembly was then cured at 80° C. for 24 hours. A dielectric reflector 30 is provided on the bottom of membrane 34.

Figure 19:
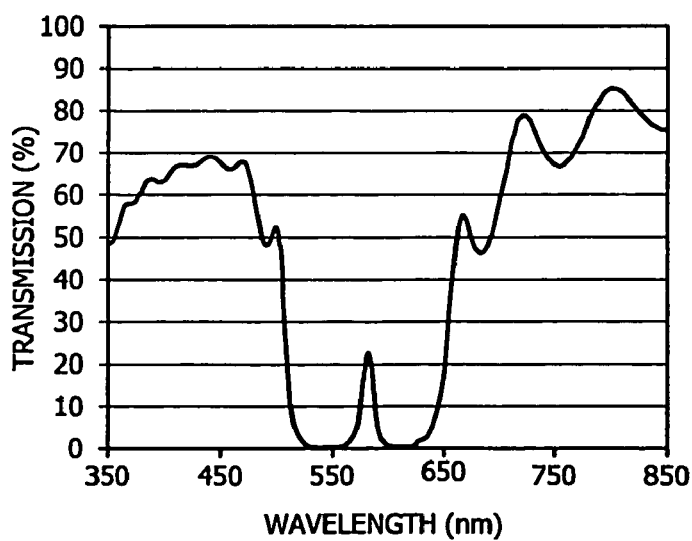
FIG. 19 is a graph of the transmission spectrum for a vertical cavity tuned to 591 nm. The full width half maximum of the cavity is much broader than the simulation, which is a result of many factors including lower mirror reflectivity, shift in mirror wavelength and loss of phase matching.

The device was tested by two distinct methods. The first method was to measure the transmission characteristics of the cavity and compare them to the simulation. The flow channels 14 were filled with water for index matching purposes and for comparison with the simulation. Since the model takes into account the concentration of the analyte, it was necessary to establish a baseline and thus water had to be tested first. The vertical cavity structure was placed inside a Shimadzu 1601 spectrophotometer with the appropriate filter holder attachment. The cavity was compared against a baseline reference of PDMS flow cell to take into account any absorption that occurs in the material. A transmission measurement was then performed from 350 nm to 850 nm and a spectrum was obtained. The transmission spectrum is shown in FIG. 19.

The second method involved placing the vertical cavity system directly on top of a 1024×1024 pixel CMOS APS sensor. Flow channels were filled with various concentrations of bromophenol blue and water for reference. The structure was illuminated from above by a $\lambda_{peak}$=588 nm AlInGaP LED operating at 3.3V forward bias. A proximity image of the structure was taken and the channels were analyzed using image processing described earlier to determine the percentage transmission compared to the water filled channels. Multiple samples were acquired and analyzed to provide adequate statistical analysis, A similar flow system without the integrated vertical cavity was also tested to provide comparison. A control curve was generated using a Shimadzu 1601 spectrophotometer.

Table 2 summarizes the results for the tested device, the cavity-less structure, and control transmission percentage versus concentration. As can be seen, the vertical cavity structure shows significant improvement over the cavity-less system in terms of determining concentration. It can also be seen that the vertical cavity system has very similar performance to the Shimadzu spectrophotometer which has a path length of 1 cm.

By testing the devices, a figure of merit which describes the enhancement can be determined. The most direct method for measuring the enhancement is to compare the lowest detectable concentration with the cavity versus without the cavity. From the experiments conducted, the greatest enhancement measured was approximately 30, although the typical value for enhancement was around 10. The system unfortunately suffers from very strict fabrication tolerances and imperfections in fabrication typically lower the enhancement. It should also be noted from Table 2 that the minimum detectable concentration of 500 nM has a relatively large error bar. This is due to the inconsistency in the measurements made for that concentration. At such low concentrations it is very difficult to distinguish the analyte under test from the water reference.

TABLE 2

Transmission measurements normalized for maximum transmission and path length

|  | Vertical Cavity | Non-cavity | Control |
|---|---|---|---|
| 500 nM Bromophenol Blue | 99.985 +/− .005% | n/a | 99.987% |
| 1 μM Bromophenol Blue | 99.971% | n/a | 99.974% |
| 5 μM Bromophenol Blue | 99.870% | n/a | 99.872% |
| 10 μM Bromophenol Blue | 99.750% | n/a | 99.744% |
| 30 μM Bromophenol Blue | 99.237% | 99.239% | 99.235% |
| 50 μM Bromophenol Blue | 98.725% | 98.498% | 98.729% |
| 100 μM Bromophenol Blue | 97.41% | 96.689% | 97.474% |

Although only one specific substance was tested, the system can easily be created to work with any specific wavelength or a multitude of wavelengths. With this feature, miniaturized spectroscopic devices can readily be constructed. The volumes tested within the device are on the order of picoliters. Through the use of this technology multiple solutions can be tested in parallel, with a high degree of sensitivity.

In summary, a monolithic cavity enhanced microfluidic device has been developed for performing absorption spectroscopy. The integration of a vertical cavity allows for much lower concentrations of solutions to be analyzed than was previously published with our monolithic spectrometer. The vertical cavity enhancement allows for the device to compensate for some of the loss of path length that is associated with using microfluidic systems for spectroscopy.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments. For example, the vertical cavity can be replaced by horizontal cavities that are microfabricated at the bottom of the flow channels, e.g. whispering gallery mode cavities, such as disks or rings, or Bragg reflection cavities such as photonic crystals or gratings.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A miniaturized fluidic spectrometer comprising:
    a broadband light source where a fluorescent spectrum is obtained from an excitation frequency provided by the light source;
    a fluidic circuit illuminated by the light source having a plurality of flow channels defined therein through which at least one analyte flows;
    a proximity detector array disposed below and aligned with the fluidic circuit for detecting light intensity from the light source transmitted through the fluidic circuit, including through the flow channels in which the at least one analyte flows;
    a variable filter disposed between the detector array and the fluidic circuit so that each position of the detector array is provided with a different wavelength response thereby providing a hyper-spectral imaging array;
    a blocking filter to reduce the excitation frequency from the detector array, while permitting transmission of an emission frequency,
    wherein the blocking filter is characterized by a varying spectral position of the reflectivity edge; and
    a processor to geometrically normalize the light to the filter characteristics and to spectrally normalize the light source during data acquisition, and to compare each specific wavelength/area under test to a specific solvent reference flow channel in the fluidic circuit.

2. The spectrometer of claim 1 where the detector array is a CMOS imaging chip.

3. The spectrometer of claim 1 where the variable filter comprises a multilayer dielectric stack.

4. The spectrometer of claim 3 where the multilayer dielectric stack comprises a Fabry-Perot cavity.

5. The spectrometer of claim 4 where the Fabry-Perot cavity comprises a 2n+1 layer structure, a first n layers comprised of alternating layers of $Si_3N_4$ and $SiO_2$ of $\lambda/4$ thickness, a $\lambda/2$ thick layer of $SiO_2$, and n more layers alternating layers of $Si_3N_4$ and $SiO_2$ of $\lambda/4$ thickness.

6. The spectrometer of claim 1 where the variable filter is grown on the fluidic circuit.

7. The spectrometer of claim 1 where the detector array is an analog or digital imager.

8. The spectrometer of claim 1 further comprising a lens between the light source and the detector array.

9. The spectrometer of claim 1 further comprising a flow cytometer for fluorescence and/or absorption activated cell sorting.

10. The spectrometer of claim 1 where the light source comprising an LED array and further comprising a high finesse optical cavity filter defined on LED array, which optical cavity filter is disposed directly on the fluidic circuit, which in turn is disposed on the detector array.

11. The spectrometer of claim 1 further comprising a microfabricated vertical or horizontal cavity in which the fluidic circuit is disposed.

12. The spectrometer of claim 11 where the vertical cavity comprises an optimized Fabry-Perot etalon.

13. The spectrometer of claim 11 where the fluidic circuit is defined in an elastomeric material and further comprising means for tuning the Fabry-Perot etalon by pressurization of flow channels in the elastomeric material.

14. A method of performing spectroscopy with a CMOS detector array comprising:
   radiating broadband light onto a towing analyte in a fluidic circuit;
   variably filtering the light between the CMOS detector array and the fluidic circuit so that each position of the CMOS detector array is provided with a different wavelength response;
   normalizing the light to the filter characteristics and spectrally normalizing the light source during data acquisition;
   comparing each specific wavelength/area under test to a specific solvent reference flow channel in the fluidic circuit;
   obtaining a fluorescent spectrum from an excitation frequency provided by the light source;
   reducing the excitation frequency from the detector array, while permitting transmission of an emission frequency;
   varying the spectral position of the reflectivity edge; and
   detecting transmission or absorbance of the light through flowing analyte using the CMOS proximity detector array disposed below the fluidic circuit, thereby providing a hyper-spectral imaging array.

15. The method of performing spectroscopy of claim 14 further comprising increasing the optical path length of light in the analyte in a fluidic circuit by multiply reflecting the light transmitted through the fluidic circuit before detecting transmission or absorbance of the light.

16. A method of performing spectroscopy with a detector array comprising:
   radiating light onto a flowing analyte in a fluidic circuit;
   increasing the optical path length of light in the analyte in a fluidic circuit by multiply reflecting the light transmitted through the fluidic circuit before detecting transmission or absorbance of the light;
   normalizing the light to the filter characteristics and spectrally normalizing the light source during data acquisition;
   comparing each specific wavelength/area under test to a specific solvent reference flow channel in the fluidic circuit;
   obtaining a fluorescent spectrum from an excitation frequency provided by the light source;
   reducing the excitation frequency from the detector array, while permitting transmission of an emission frequency;
   varying the spectral position of the reflectivity edge; and
   detecting transmission or absorbance of the light through flowing analyte using the detector array disposed below the fluidic circuit.

* * * * *